United States Patent
Helmig et al.

(10) Patent No.: US 9,808,649 B2
(45) Date of Patent: Nov. 7, 2017

(54) IMMOBILIZATION SYSTEM TO SUPPORT AN IN VIVO MEDICAL DEVICE

(71) Applicant: Medical Tool & Technology, LLC, Hawthorne, FL (US)

(72) Inventors: Richard David Helmig, Hawthorne, FL (US); John Scott Wheeler, Bel Air, MD (US)

(73) Assignee: MEDICAL TOOL & TECHNOLOGY, LLC, Hawthorne, FL (US)

( * ) Notice: Subject to any disclaimer, the term of this patent is extended or adjusted under 35 U.S.C. 154(b) by 0 days.

(21) Appl. No.: 15/399,805

(22) Filed: Jan. 6, 2017

(65) Prior Publication Data
US 2017/0197092 A1   Jul. 13, 2017

Related U.S. Application Data

(60) Provisional application No. 62/387,833, filed on Jan. 7, 2016.

(51) Int. Cl.
*A61N 5/10*   (2006.01)
*A61F 5/37*   (2006.01)

(52) U.S. Cl.
CPC .............. *A61N 5/10* (2013.01); *A61F 5/3776* (2013.01); *A61N 5/1016* (2013.01); *A61N 2005/1012* (2013.01); *A61N 2005/1097* (2013.01)

(58) Field of Classification Search
CPC .................... A61N 5/10; A61N 5/1016; A61N 2005/1012; A61N 2005/1097; A61F 5/3776

(Continued)

(56) References Cited

U.S. PATENT DOCUMENTS 5,295,945 A * 3/1994 Miller .................. A61N 5/1016
                                                     2/406
5,947,891 A * 9/1999 Morrison ............. A61N 5/1016
                                                     600/6

(Continued)

OTHER PUBLICATIONS

DM Medical, Radiation Implant Brief Model M-100 Instructions, Aug. 29, 2008 (see attached).*

(Continued)

*Primary Examiner* — Navin Natnithithadha
*Assistant Examiner* — Sunita Reddy
(74) *Attorney, Agent, or Firm* — Saliwanchik, Lloyd & Eisenschenk

(57) ABSTRACT

The problem of securing the position of an internally placed medical device that extends out of the body during targeted high-dose-rate (HDR) brachytherapy is solved by a uniquely configured immobilization system that can be utilized to stabilize medical devices placed, for example, within the uterus or cervix. During the process of transporting a patient from the location where the HDR applicator is emplaced, for example, where the tandem and ring is placed within the cervix of a patient, to the location where the treatment is actually applied to the tissue, the medical device can move out of place and in so doing cause discomfort, pain, or an ineffective treatment for the patient. The embodiments of this immobilization system can include a strap apparatus, a straddling girdle, and bracket that can be attached to a patient. This immobilization system ensures the position of an internally placed medical device during targeted HDR brachytherapy.

18 Claims, 12 Drawing Sheets

(58) Field of Classification Search
USPC .................................. 600/1–6; 128/897–899
See application file for complete search history.

(56) References Cited

U.S. PATENT DOCUMENTS

| | | | | |
|---|---|---|---|---|
| 6,129,670 | A * | 10/2000 | Burdette | A61B 34/20 600/427 |
| 6,390,968 | B1 * | 5/2002 | Harmon | A61N 5/1016 600/6 |
| 6,512,942 | B1 * | 1/2003 | Burdette | A61B 34/20 600/3 |
| 2003/0028067 | A1 * | 2/2003 | Tarone | A61N 5/1007 600/1 |
| 2003/0153803 | A1 * | 8/2003 | Harmon | A61N 5/1016 600/6 |
| 2003/0229282 | A1 * | 12/2003 | Burdette | A61B 34/20 600/439 |
| 2004/0059177 | A1 * | 3/2004 | Baltas | A61N 5/1007 600/3 |
| 2007/0225544 | A1 * | 9/2007 | Vance | A61N 5/1027 600/8 |
| 2008/0021257 | A1 * | 1/2008 | Roychowdhury | A61N 5/1001 600/3 |
| 2008/0064916 | A1 * | 3/2008 | Mick | A61N 5/1016 600/6 |
| 2010/0048978 | A1 * | 2/2010 | Sing | A61N 5/1016 600/6 |
| 2010/0067659 | A1 * | 3/2010 | Bush | A61B 6/0435 378/68 |
| 2010/0152520 | A1 * | 6/2010 | Mick | A61N 5/1016 600/6 |
| 2011/0230700 | A1 * | 9/2011 | Sing | A61N 5/1015 600/7 |
| 2012/0022314 | A1 * | 1/2012 | Sing | A61B 90/39 600/3 |
| 2012/0123188 | A1 * | 5/2012 | Rahimian | A61B 17/0206 600/6 |
| 2012/0277518 | A1 * | 11/2012 | Mick | A61N 5/1016 600/6 |
| 2013/0053682 | A1 * | 2/2013 | Esthappan | A61N 5/10 600/411 |
| 2013/0096422 | A1 * | 4/2013 | Boctor | A61B 5/0095 600/424 |
| 2013/0209208 | A1 * | 8/2013 | Bailey | B25J 11/00 414/728 |
| 2014/0257013 | A1 * | 9/2014 | D'Andrea | A61N 5/1002 600/2 |
| 2015/0190621 | A1 * | 7/2015 | Yeung | A61M 29/02 600/7 |
| 2015/0306425 | A1 * | 10/2015 | Bharat | G06T 7/70 382/128 |

OTHER PUBLICATIONS

Radiation Implant Brief product information, [online, webpage, retrieved Mar. 27, 2015] from: http://www.rpdinc.com/radiation-implant-briefs-4635.html, p. 1.

* cited by examiner

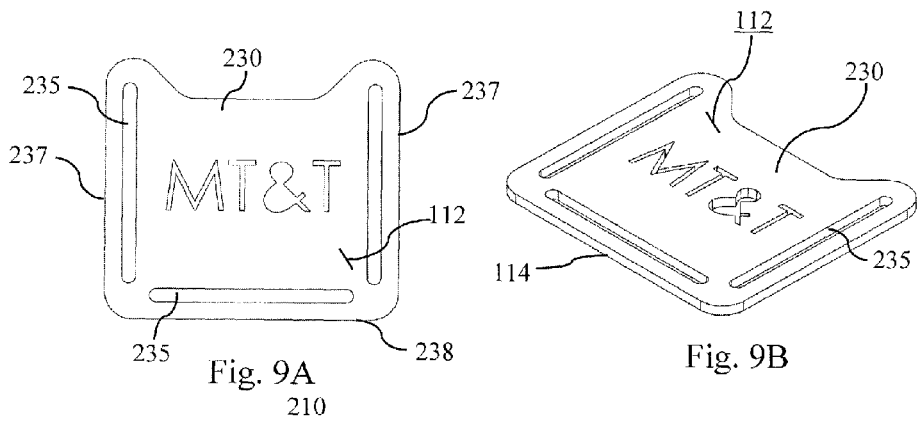
Fig. 9A
Fig. 9B
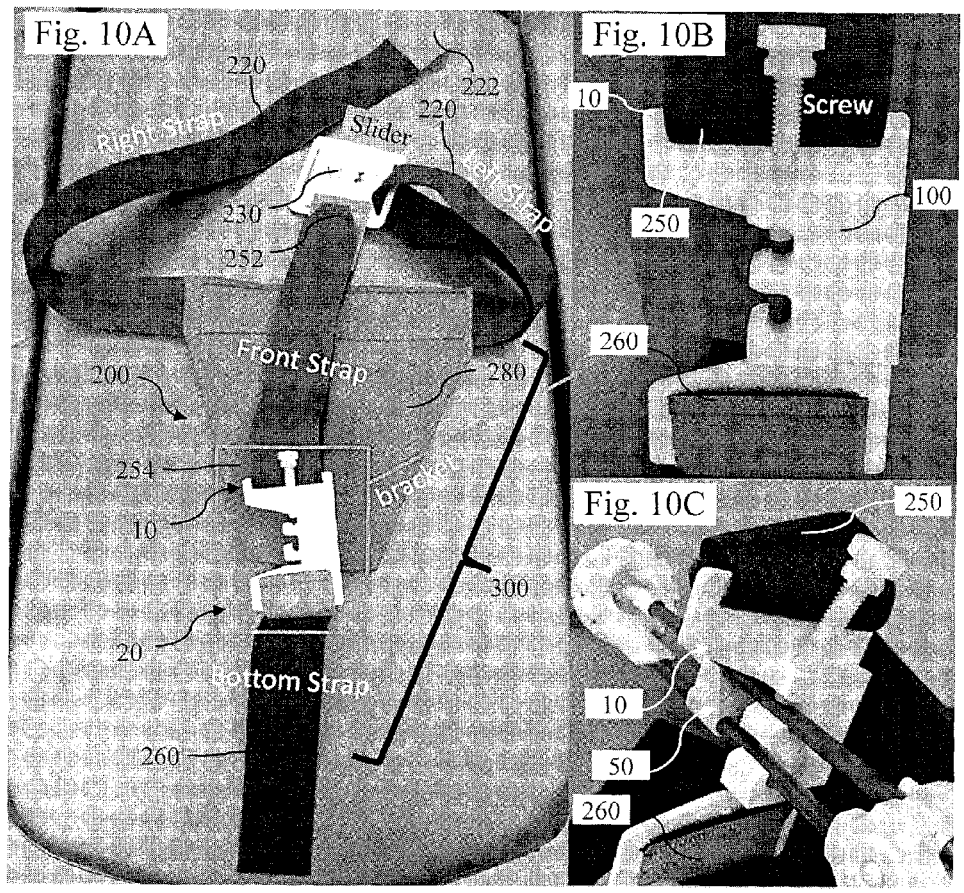
Fig. 10A
Fig. 10B
Fig. 10C

IMMOBILIZATION SYSTEM TO SUPPORT AN IN VIVO MEDICAL DEVICE

CROSS-REFERENCE TO A RELATED APPLICATION

This application claims the benefit of U.S. Provisional Application Ser. No. 62/387,833, filed Jan. 7, 2016, the disclosure of which is hereby incorporated by reference in its entirety, including all figures, tables and drawings.

BACKGROUND OF INVENTION

Many medical treatment methodologies require the temporary in vivo placement of one or more devices. This can allow treatment to be applied to specific areas within the body, which can be particularly beneficial when the treatment material or substance is toxic, radioactive, or otherwise dangerous to healthy tissues. By targeting just those tissues that require treatment, it can protect healthy tissue and often minimizes the side-effects elicited by many treatment regimens.

One example of this type of targeted treatment is high-dose-rate (HDR) brachytherapy, which is extensively used as a boost treatment for cervical cancer. The procedure involves the in vivo placement of a radiation source close to a tissue that is to receive radiation treatment. When utilized for treatment of cervical cancer, a common applicator for HDR brachytherapy is a tandem and ring device, which has round hollow holders, in which the radiation source can dwell and radiate through. These holders can be placed in vivo adjacent to the cervix so that the radiation is targeted, as much as possible, at the site of the cancer lesion.

For HDR brachytherapy and other similar types of treatments to be efficient and minimize radiation or other substances from affecting surrounding healthy tissues, it is important for the medical device, e.g., tandem and ring, to remain in optimal placement. However, during the process of transporting a patient from the location where the medical device is emplaced, for example, where the tandem and ring is placed within the cervix of a patient, to the location where the treatment is actually applied to the tissue, the medical device can move out of place and in so doing cause discomfort or pain to the patient. This movement can also cause the radiation or other treatment substance to be applied ineffectively to the lesion site or cause it to be applied to the wrong tissues.

There is a need for a companion device that can secure the position of an internally placed medical device, so that movement of the patient does not adversely affect the placement of the device. There is, in particular, a need for a device that can secure the position of a tandem and ring device in the cervix during transport of a patient between locations.

BRIEF SUMMARY

The embodiments of the subject invention successfully address the above described disadvantages associated with the use of internally placed medical devices and can increase the efficacy and safety of these devices by stabilizing them in the body to inhibit dislocation. In particular, the subject invention provides a uniquely configured immobilization system that can be utilized to stabilize medical devices placed within the uterus or cervix that extend out of the uterus. In a specific embodiment, the subject invention provides a system by which a tandem and ring device for HDR brachytherapy treatment can be effectively secured after optimal placement within the patient uterus and against the cervix. Embodiments of the immobilization system, according to the subject invention, can include a strap apparatus, such as, for example, a straddling girdle, and a bracket that can be attached to a patient. The strap apparatus can be used to secure the position of the bracket on a patient body. The bracket can be configured to connect or attach to one or more structures on the medical device that extend from the body opening or cavity. In a particular embodiment, the bracket is configured to receive one or more posts or the hollow rods that support components of a tandem and ring device.

A bracket embodiment of the subject invention can be a rigid or semi-rigid plate that has one or more receivers in which some part of the medical device extending from the uterus or other body cavity can be received and supported against or relative to the body. In a specific example, a bracket can have one or more receivers in which the hollow posts of a tandem and ring device can be positioned and secured. Other embodiments have a more general or universal receiver in which many different types of medical devices, or portions thereof, can be received and secured within or against the body.

A strap apparatus can be used to secure the position of the bracket on a patient. The bracket can include one or more connectors, for example, openings, to which one or more straps, bands, belts, etc. of the strap apparatus can be affixed to secure the position of the bracket to a patient. Ideally, the strap apparatus is fit closely to the body so that the bracket to which it is attached is also held securely against the body. In particular, the strap apparatus is configured as a strapping girdle with one or more straps that can be wrapped around the body and/or the waist to secure the bracket against the perineum area.

Once a medical device or part thereof has been positioned with one or more receivers of a bracket secured against the body, it can be advantageous for the receiver to further have a brace that can inhibit the medical device from sliding or otherwise moving within the receiver. For example, on a tandem and ring device there are one or more hollow tubes that can be secured within one or more receivers of a bracket. The use of one or more braces with a receiver can ensure that the hollow tubes not only remain in proper alignment within the body, but also do not slide out of the body. Thus, a brace can have an operable connection with the receiver so as to make direct or indirect contact with the medical device.

It should be noted that this Brief Summary is provided to generally introduce the reader to one or more select concepts described below in the Detailed Disclosure in a simplified form. This Summary is not intended to identify key and/or required features of the claimed subject matter. Other aspects and further scope of applicability of the present invention will also become apparent from the detailed descriptions given herein. It should be understood, however, that the detailed descriptions, while indicating preferred embodiments of the invention, are given by way of illustration only, since various changes and modifications within the spirit and scope of the invention will become apparent from such descriptions. The invention is defined by the claims below.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIG. 4A is a top plan view and FIG. 4B is a side left side perspective view, and FIG. 1C is a left side elevation view.

FIG. 3C also illustrates an alternative embodiment of a connector.

FIG. 6A is an anterior end perspective view, FIG. 6B is a top plan view, FIG. 6C is a dorsal end bottom perspective view, and FIG. 6D is a left side elevation view.

FIG. 7A is a top plan view and FIG. 7B is a dorsal end perspective view.

FIGS. 9A-9B illustrate an embodiment of a buckle that can be used with certain embodiments of a strapping girdle.

FIGS. 10A-10C are photographs showing one embodiment of a strapping girdle utilized with a buckle (FIG. 10A) and how the straps of the strapping girdle can be attached through the slits in a bracket. FIG. 10C shows an example of how a tandem and ring device can be attached and secured to a bracket embodiment of the subject invention.

DETAILED DISCLOSURE

Figure 1B:
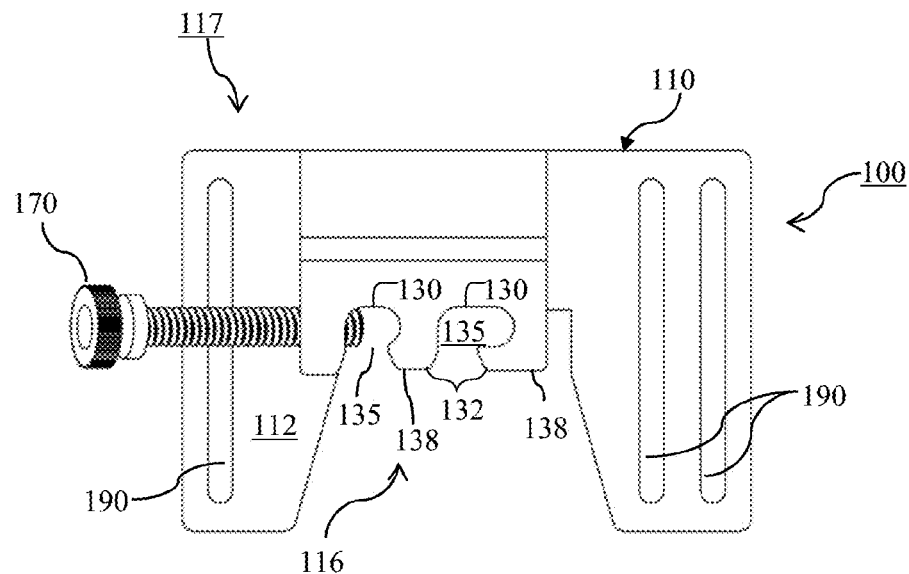
FIGS. 1A-1C illustrate the embodiment in FIGS. 2A-2B with a brace that is through screw emplaced on the bracket, where
Figure 1A:
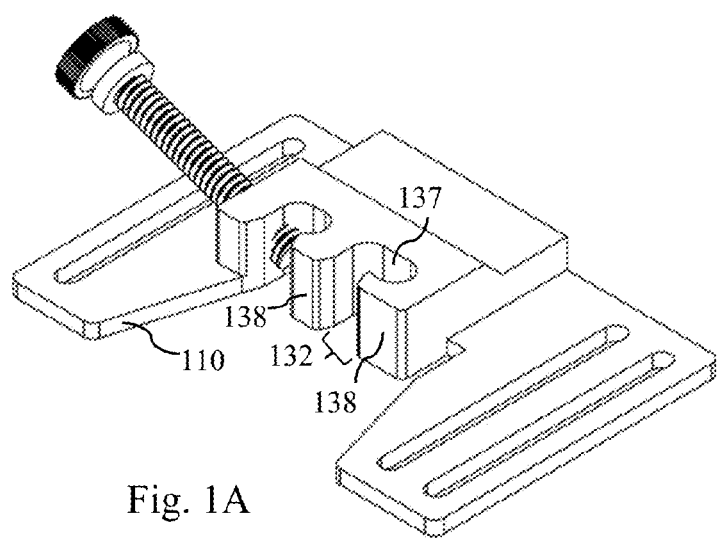
Figure 1C:
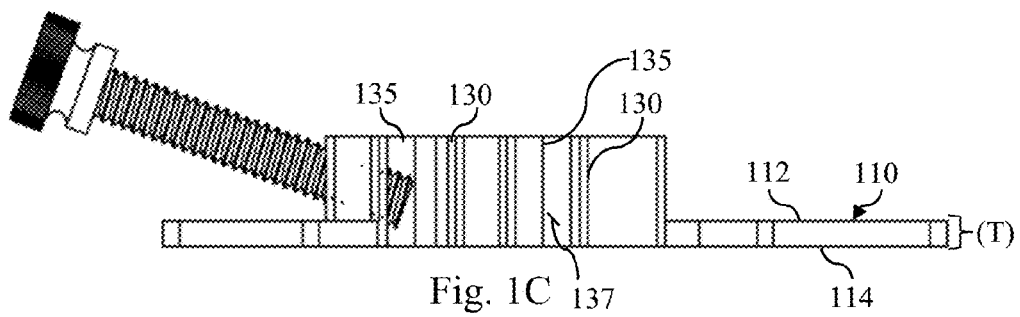

The embodiments of the subject invention pertain to an immobilization system for attachment to a device, such as a medical device, placed at least partially in vivo. More specifically, the subject invention provides one or more embodiments of a bracket and strap apparatus that can be affixed around a patient to secure and stabilize a medical device extending from or protruding from a cavity or opening in the body. Specific embodiments can secure and stabilize an in vivo placed device. In one embodiment, the bracket has a configuration particularly suited to securing and stabilizing an in vivo positioned tandem and ring device. In another embodiment, the bracket has a more universal design that can be used to secure any of a variety of in vivo placed devices.

The following description will disclose that embodiments of the subject invention are particularly useful for in vivo medical treatments or procedures, in particular brachytherapy devices used for procedures or treatment in and around the perineum area of the body, including those in the uterine or cervical cavities. However, uses for securing devices outside or on the body are also possible and modifications to affect such uses are within the scope of this invention. A person with skill in the art will be able to recognize numerous other uses that would be applicable to the devices and methods of the subject invention. While the subject application describes, and many of the terms herein relate to, a use for high-dose radiation brachytherapy, modifications for other uses will be apparent to a person with skill in the art and having benefit of the subject disclosure and are within the scope of the present invention.

The terms "perineum" and "groin" are used interchangeably herein to refer to that general area of the body located between the legs of a human male or human female patient. These terms are used merely for literary convenience to refer to a general area of the body where a bracket embodiment of the subject invention can be positioned. It will be appreciated that the bracket embodiments described herein could be used in other areas of the body. Thus, these terms are not intended to limit the subject invention in any way.

The term "medical device" as used herein is also for literary convenience. As used herein, a "medical device" can be any device that has surfaces that contact blood or other bodily tissues in the course of their operation. This can include, for example, brachytherapy devices, surgical tools, objects, or instruments used for a treatment or surgery on a patient. More particularly, it can pertain to medical devices that, when in use, have some portion that remains outside of the body or a body cavity, with which embodiments of the subject invention can be cooperatively engaged, as described herein.

Finally, reference is made throughout the application to the "anterior end" and "posterior end," as well as the "left side" and "right side." As used herein, the proximal end is that end, when secured to a patient, which is directed towards or nearest to the anterior side (or face side) of a patient. Conversely, the posterior end is that end, when secured to a patient, which is directed towards or nearest to the distal side (or back side) of a patient. Further, in certain embodiments, the right side is that side on which the one or more receiving slots of an embodiment of a bracket can be accessed. The left side is generally opposite to the right side and, in certain embodiments, does not allow access to the receiving slots. For the purposes of this description, the left and right sides correspond to the left and right side of a patient on which the bracket is placed. It should be understood that the left and right sides could be reversed, such that the receiving slots could be accessed from the left side of the device. Also, these terms are not meant to limit the invention in any way. They are used merely for literary convenience to orient the reader with regard to the various components or areas of the invention. A person with skill in the art will understand that if the bracket is used in another area of the body, these terms of orientation may not be accurate. But, as used herein the terms provide a clear understanding of the structure and method of using the immobilization system, regardless of where it is used on or in the body.

Reference will be made to the attached figures on which the same reference numerals are used throughout to indicate the same or similar components. With reference to the attached figures, which show certain embodiments of the subject invention, it can be seen that the immobilization system 20 of the subject invention generally comprises a bracket 100 and a strap apparatus 200, specifically, a straddling girdle, that can be used to adequately immobilize the bracket on a patient.

The bracket can have a plate 110 with one or more receivers 130 to which a medical device 50 can be secured. As will be described, a receiver can be configured to accept within a channel 135 a specific type of medical device or the receiver can be universal to accept any of multiple types of medical devices. A brace 170 can be used in conjunction with a receiver to secure the medical device 50 or some part thereof in the receiver to inhibit rotation and translation of the medical device. There can further be one or more connectors 190 on or in the bracket with which the strap apparatus or strapping girdle can be affixed.

The strap apparatus 200 in the form of a straddling girdle 210 can have, in general, a waist strap 220, an anterior straddling strap 250, and a posterior straddling strap 260 that extend from the waist strap and between the patient's legs that can each be affixed to the bracket by one or more connectors 190. There can be an optional posterior pad 280 that can assist in placing and holding the straps in position on a patient. The straps, once secured on the patient, can hold the bracket and any medical device affixed thereto as positioned within the patient. Ideally, the straddling girdle and bracket that provide the immobilization system 300 are placed so that even if the patient moves, an in vivo placed medical device will remain adequately in place.

With regard to the bracket, it can be seen in the figures, particularly FIGS. 1A-1C and 5A-5B, that embodiments include a plate 110 that has a front side 112 and a backside 114, a right side 116 and a left side 117. The backside 114 can contact the patient and is designed to be comfortable when placed against the skin or body and easily removed after use. The shape of the plate and bracket can vary and should be conducive to placement over the perineum and between the legs. In one embodiment, there can be one or more cut-outs 115 on a plate that can accommodate a patient's shape or body configuration. FIGS. 5A-5B, 6A-6D illustrate a non-limiting example of a plate having cut-outs 115 on the left and right side. A person with skill in the art would recognize that other ergonomic features can be incorporated into the plate, such as, for example, one or more curves on the backside, different circumferential shapes, e.g., triangular, oval, round, or other polygonal shape, surface extensions that facilitate holding the bracket in place against the body, beveled or smoothed edges, and other features known to those with skill in the art.

The thickness of the plate is generally not a limiting factor. As long as the material(s) utilized provide sufficient rigidity to the plate and/or the bracket to stabilize the bracket and a medical device deployed therein. In general, it can be beneficial for the thickness to be minimal, for a variety of reasons understood to those with skill in the art. However, as will be discussed below, one or more receivers 130 on the plate can have channel walls 137 that provide a specific thickness (T) that allows for use of certain braces 170. Thus, the plate can have the same thickness as the one or more receivers. This is not, however, required and the plate can have a thickness that is less than that of a receiver. It is also possible for a plate to have variable thickness, such that the plate is thicker in certain areas than in other areas. Such variations in the plate configuration, which provide the same function, in substantially the same way, with substantially the same result are within the scope of this invention.

Likewise, the other dimensions of a plate are not a limiting factor, accept that they should not preclude the device being positioned against the perineum of a patient.

Figure 11A:
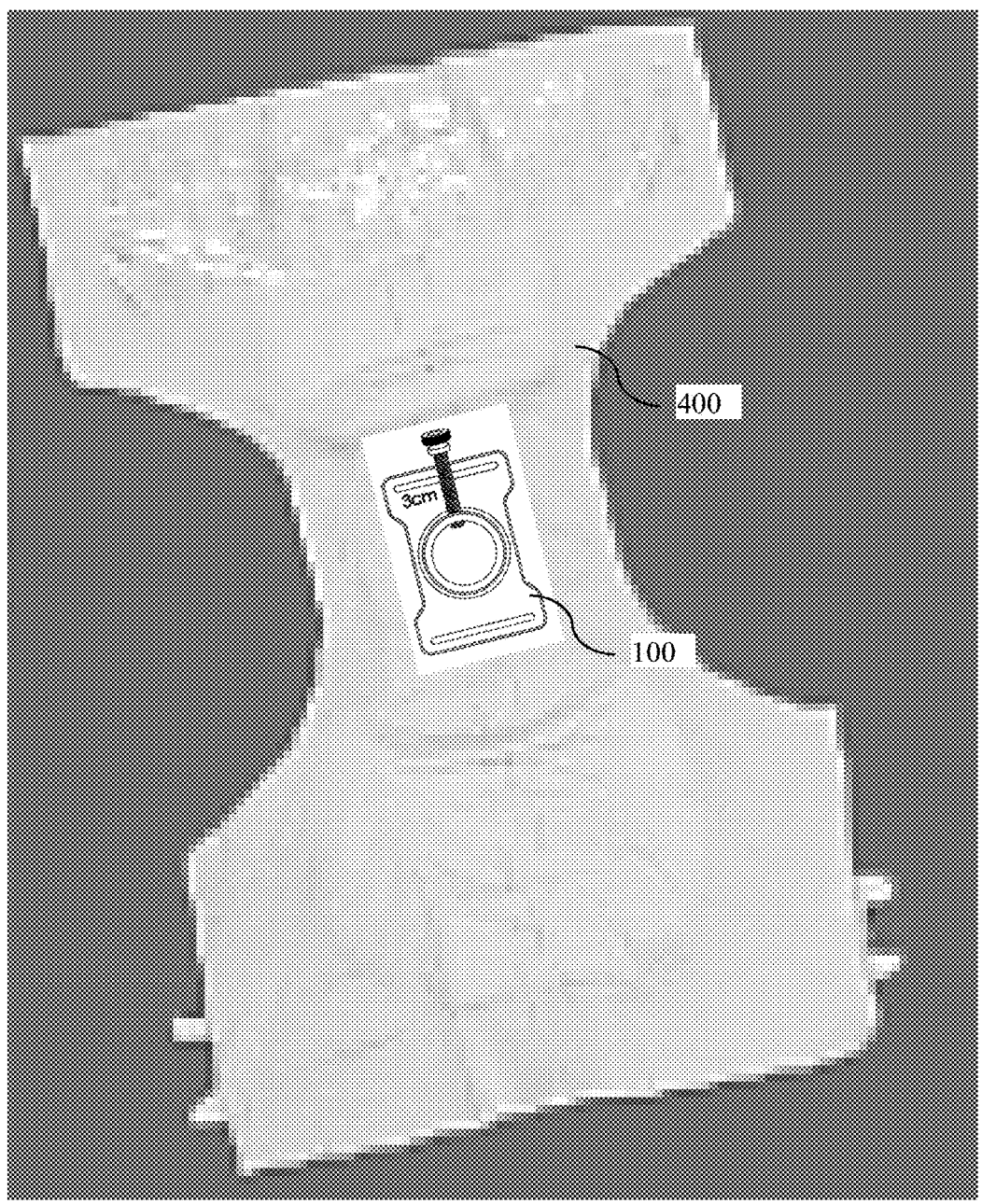
FIGS. 11A, 11B, 11C and 11D illustrate alternative embodiments that utilize garments to secure a bracket in place on a patient.

In one embodiment, the plate 110 can be positioned against the perineum of the patient and can stabilize and support one or more receivers 130. A receiver can accept a medical device, or some part thereof, so as to secure it within or on a patient. One or more receivers 130 can be affixed to or structurally incorporated as part of the plate. A receiver can have the same or greater thickness than the plate. In one embodiment, a receiver is designed to have at least one slot 132 that leads into a channel 135 defined by channel walls 137, where the slot opens into the channel and onto an exterior of the channel wall, such that the slot forms a passage into the channel. The slot can accept therethrough a specific type or part of a medical device or it can be more generic in shape, so as to accept any of a variety of medical devices or some part thereof. A slot and a channel can have any of a variety of shapes to accommodate medical devices, and the various shapes of each one can secure the medical device in the channel, can allow for adjustment of the medical device, can permit adjustment of its position within a patient, and provide other functions. Furthermore, each receiver in a bracket can have the same or can have different dimensions. FIG. 11A illustrates an example where one receiver is longer than the other receiver in the bracket. It is within the skill of a person trained in the art to determine an appropriate size, shape, or configuration of a slot and/or channel for any medical device to be used with a bracket 100 embodiment of the subject invention. Such variations are within the scope of this invention. The use of various braces 170, described below, can be at least one deciding factor in the thickness of a receiver.

Figure 3A:
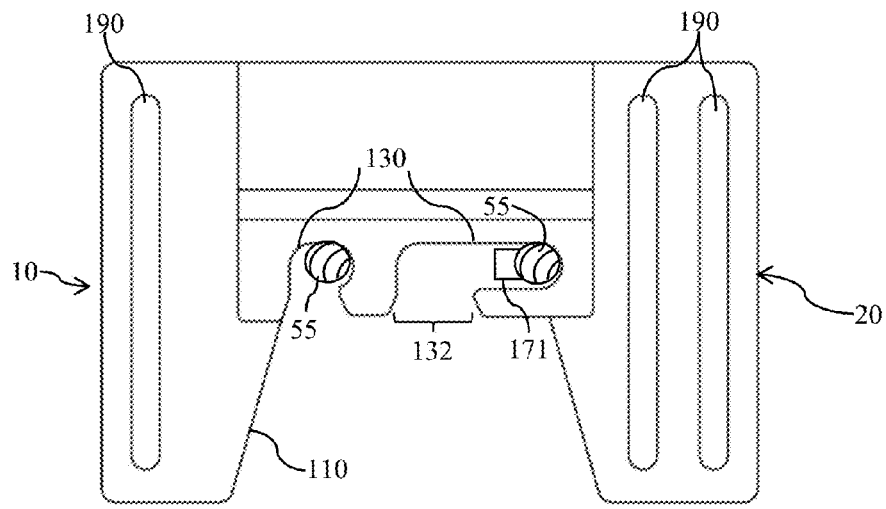
FIGS. 3A, 3B and 3C illustrate embodiments where one receiving slot is elongated for receiving tandem and ring devices of different sizes or configuration.
Figure 3B:
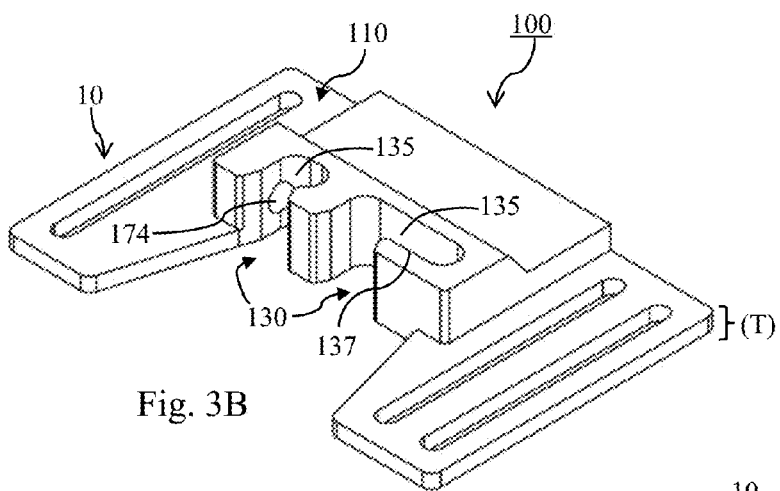
Figure 3C:
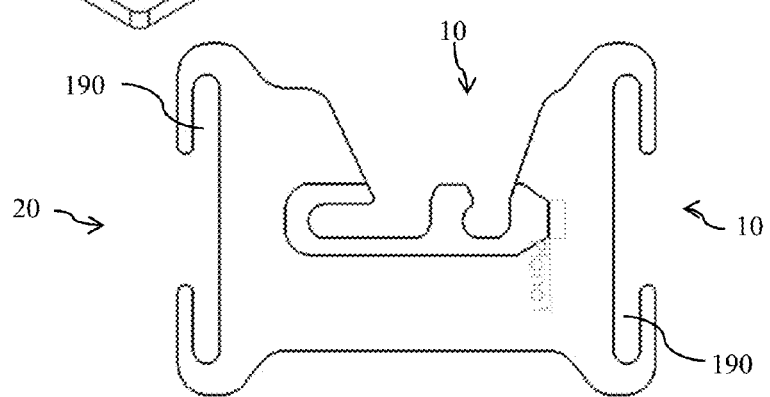
Figure 4:
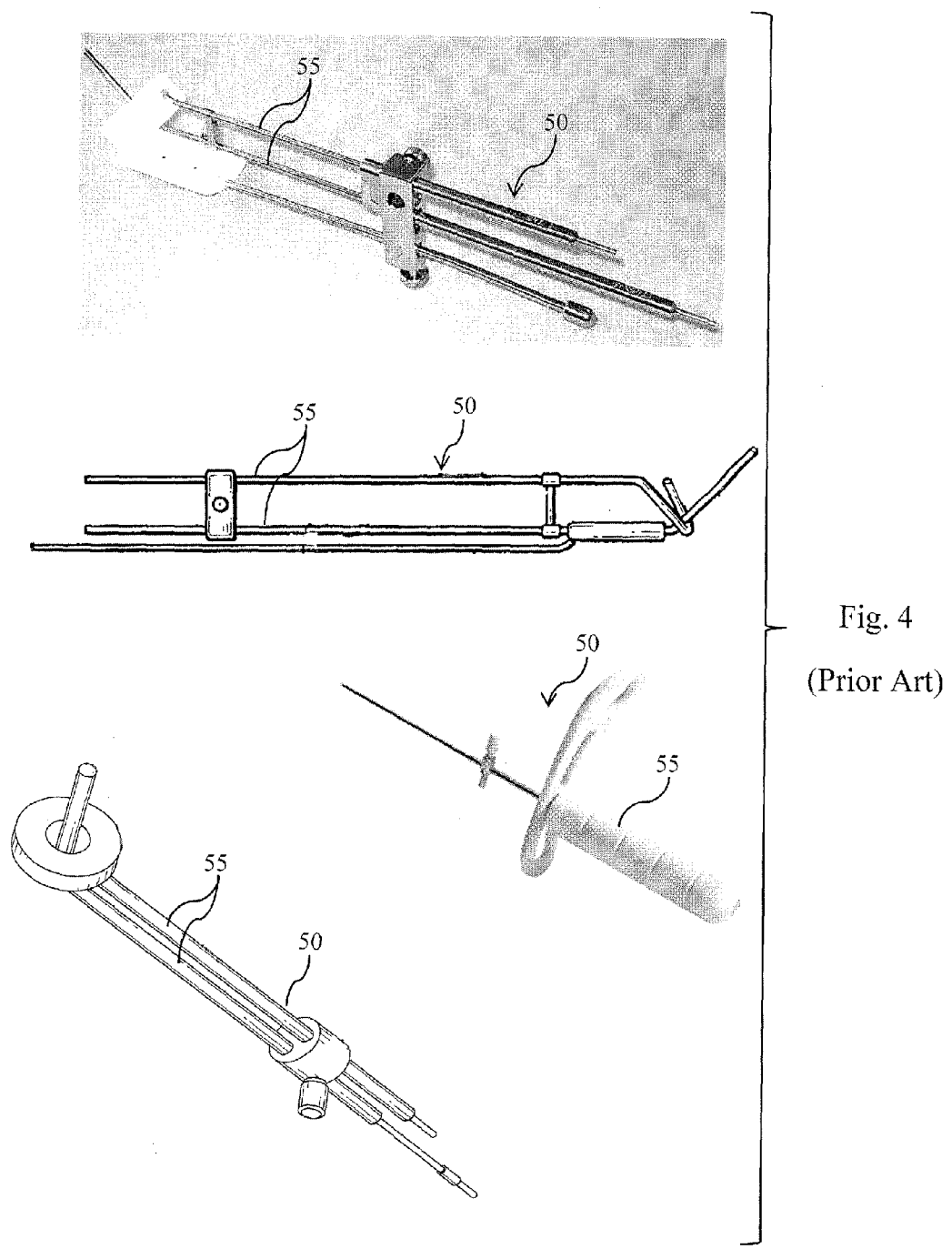
FIG. 4 illustrates non-limiting examples of tandem and ring devices that can be used with the embodiments of the subject invention, shown in the above-described figures.

In a specific embodiment, shown by way of example in FIGS. 1A-3B, there are at least two receivers 130 with slots 132 leading into channels 135 that can be specifically designed to receive the hollow holders 55 of a tandem ring medical device used for brachytherapy. FIG. 4 shows examples of some tandem ring medical devices 50 that have at least two hollow holders 55 (upper three images) that can be received into the channels of receivers on a bracket. Ideally, the hollow holders are placed in the channels after the tandem ring has been placed in vivo.

Figure 2A:
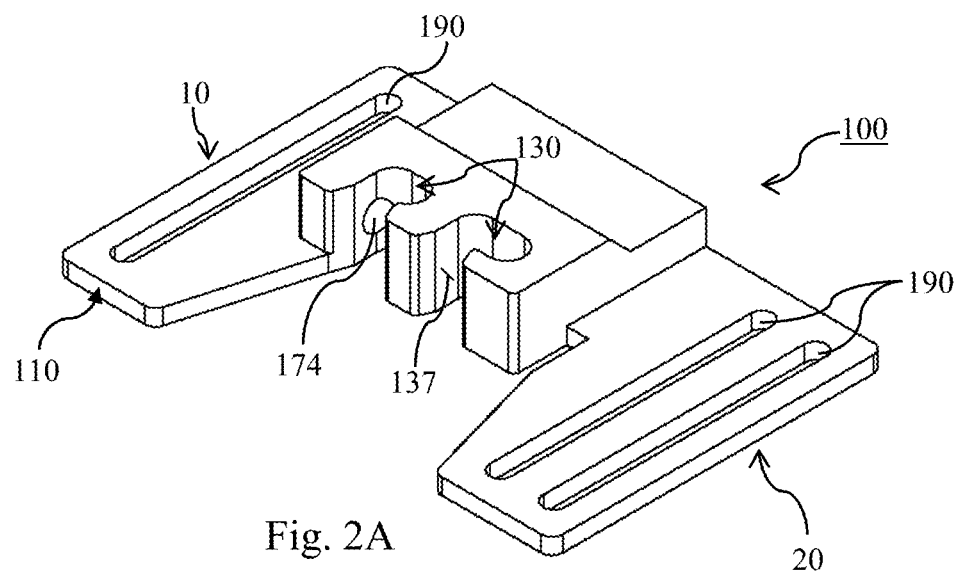
FIGS. 2A-2B illustrate a left side perspective view (FIG. 2A) and a top plan view (FIG. 2B) of one embodiment of a bracket, according to the subject invention.
Figure 2B:
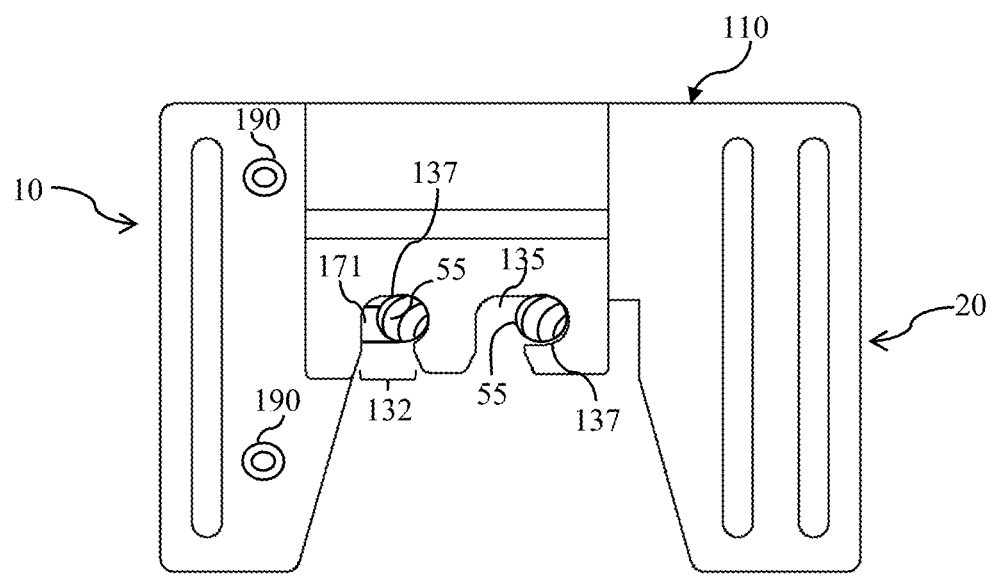

One or more of the receivers 130 can also be configured to inhibit a hollow holder from accidentally disengaging from a channel 135. In a one embodiment, a receiver can have an oblong shape with the longer side oriented from the anterior end 10 to the posterior end 20 with the slot 132 positioned closer to the anterior end, an example of which is shown in FIGS. 2B and 3A. In one embodiment, the slot and receiver channel have a L-shape configuration. With this embodiment, a hollow tube 55 can be inserted into the slot and moved or positioned towards the posterior end where the sides of the receiver will inhibit it from sliding out or otherwise leaving the channel. Alternatively, tension exerted on the hollow tube from attachment to other parts of the medical device can bias the hollow tube towards the more closed posterior end 20 of the channel, where the receiver can inhibit it from sliding out or otherwise leaving the channel.

Other types of medical devices having different shapes, purposes, or positioning can also be placed in vivo. The bottom image in FIG. 4 illustrates an example of another type of brachytherapy instrument having an entirely different design than other brachytherapy instruments seen in FIG. 4. To accommodate these and other types of instruments or devices, a more generic receiver 130 can be utilized on a bracket 110. A more generic receiver can also have a thickness (T) that is the same as or greater than the thickness of the plate. The use of various braces 170, described below, can be at least one deciding factor in the thickness of a receiver. FIGS. 5A-7B illustrate embodiments of a bracket having at least one opening through the bracket sufficiently large enough to accommodate other types or styles of medical devices. If there is more than one opening, such openings can be, but do not have to be, identical in size or shape. FIGS. 5A-7B illustrate a circular opening, but an opening can have any shape, including, but not limited to, circular, oval, square, triangular, trapezoid, combinations thereof or any other polygonal shape. As seen in FIGS. 5A-7B, the central opening can vary in size or diameter. In one embodiment, the diameter of an opening is between approximately 0.5 cm and approximately 7 cm. In a further embodiment, the diameter of an opening is between approximately 1 cm and approximately 6 cm. In a still further embodiment, the diameter of an opening is between approximately 2 cm and approximately 4 cm. In a specific embodiment, there is a single opening that is generally centralized on the bracket and has a diameter between approximately 2 cm and approximately 4 cm.

Once the bracket is secured against the perineum or groin of the patient and the medical device, or some part thereof, is positioned within one or more channels of one or more receivers, it can be preferable for the medical device to be secured in the channel to inhibit reciprocation, rotation, torque, or other movement of the medical device, relative to the bracket. This can be accomplished by any of a variety of braces 170, many known to those with skill in the art. Typically, such devices operate by at least partially closing, filling, redirecting, or minimizing the space between the medical device and one or more channel walls 137. By way of non-limiting example, a brace can be one or more plugs 171, such as shown, for example, in FIGS. 2B and 3A, which can be used to fill space between the medical device and the channel walls. A plug can, but does not have to, conform to the shape of the medical device and/or the channel. By way of another non-limiting example, a brace can be one or more set screws that extend through a threaded hole 174 in a channel wall 137, as shown, for example, in FIGS. 1A-1C, and 6A-6D. It is not unusual for medical devices to be metallic or have some metallic component thereof. Thus, by way of still further non-limiting example, a brace can be a magnetic device that secures a metallic medical device within a channel. A person with skill in the art will be able to determine other types of braces or combinations thereof for securing a medical device in a channel. Such variations which provide the same function, in substantially the same way, with substantially the same result as described herein, are within the scope of this invention.

In one embodiment, the bracket 100 is secured to the body with a strap apparatus 200. Embodiments of a strap apparatus will be discussed in more detail. With regard to the bracket, there can be one or more connectors 190 to which one or more components of a strap apparatus can be adjustably attached. For example, a connector can be a device, mechanism, or structure on the bracket that allows one or more straps of a strap apparatus, such as strapping girdle discussed below, to be adjustably attached to the bracket. The connector can also provide for permanent or removable affixation to the bracket. Ideally, the connector allows the bracket to be adjusted on a patient in either or both the posterior and anterior directions. This can allow for the optimum placement and securement of an in vivo medical device.

In one embodiment, a connector is a coupling device to which a compatible or corresponding coupling device on a strap can be attached. A coupling device can be a snap-fitting where one part of a snap is on the bracket and the other part of a snap is on the strap. FIG. 2B illustrates one example of snap-fitting components on a bracket. There are numerous types of snap-fitting or similar devices known in the art, which could be utilized with the embodiments of the subject invention. Alternatively, a coupling device can be a mechanism that connects between a strap and the bracket. For example, various types of rings, carabineers, clips, ties, zip-ties, bands, hooks, bolts, screws, toggles, and other devices for connecting a strap to a bracket could be used.

Figure 5A:
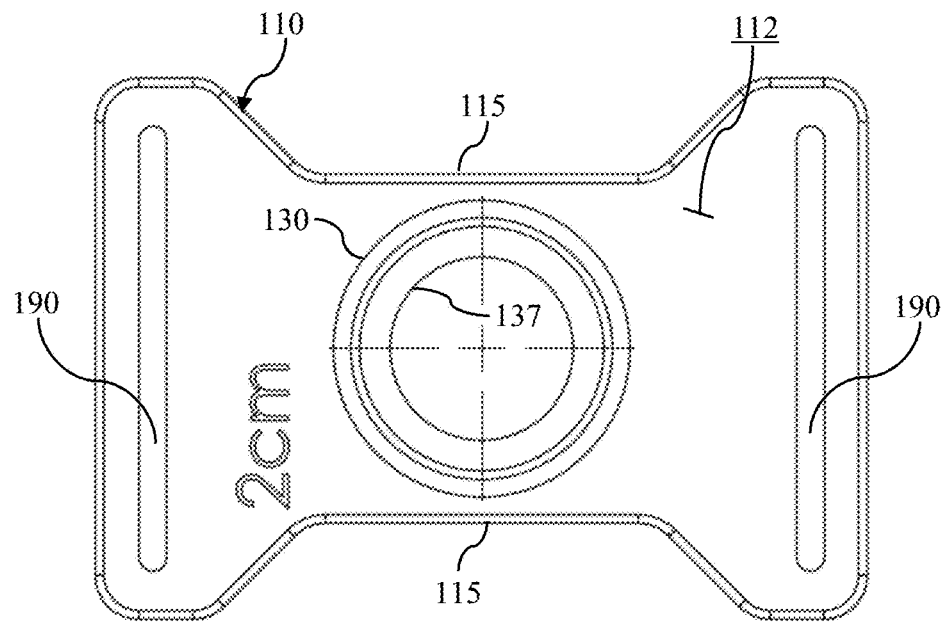
FIGS. 5A-5B illustrate an alternative embodiment of a bracket having a central orifice for receiving and securing a variety of devices that can be placed in vivo.
Figure 5B:
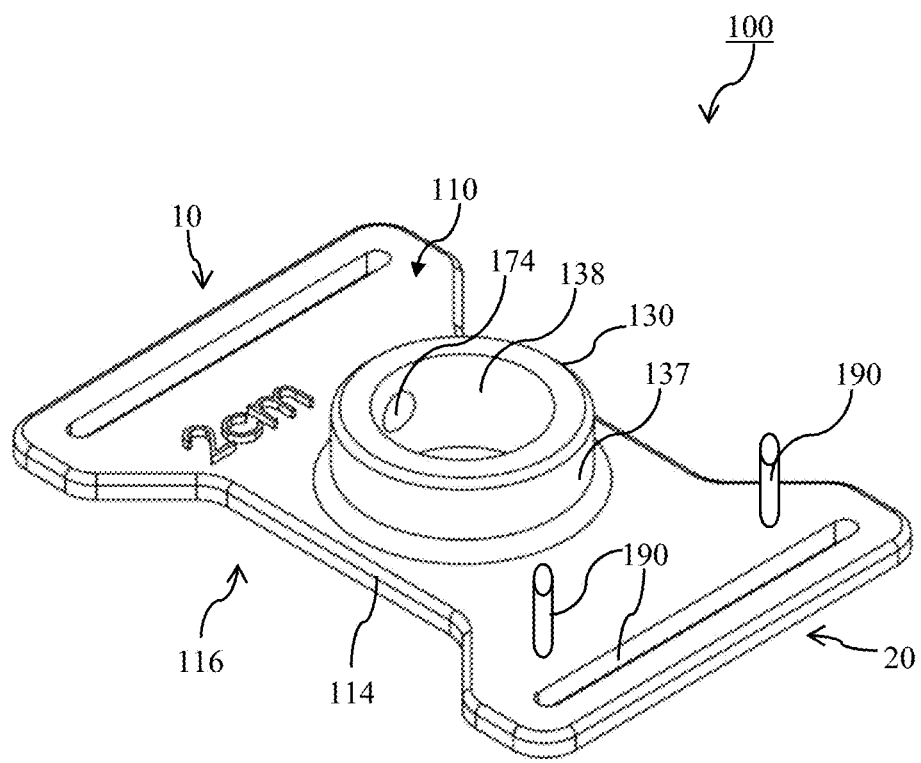
Figure 6A:
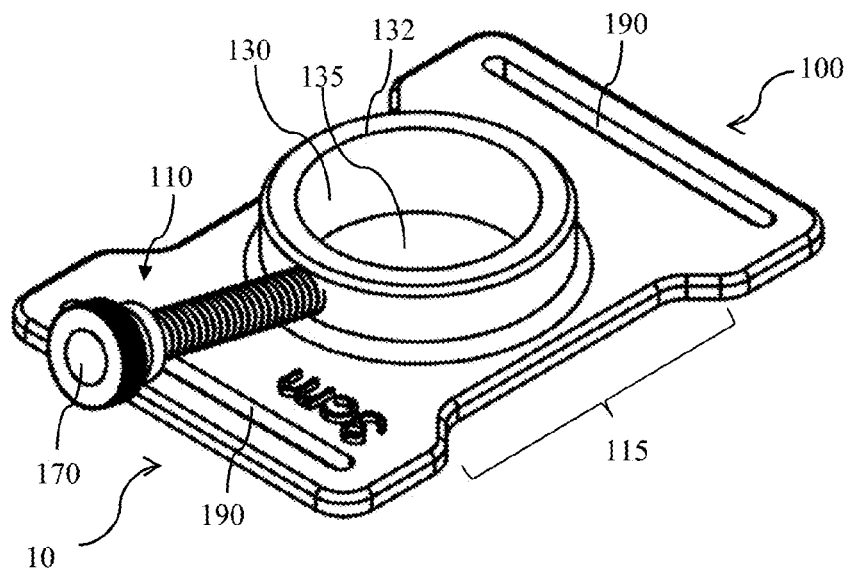
FIGS. 6A-6D illustrate an alternative embodiment, similar to that shown in FIGS. 5A-5B, with a larger orifice, where
Figure 6B:
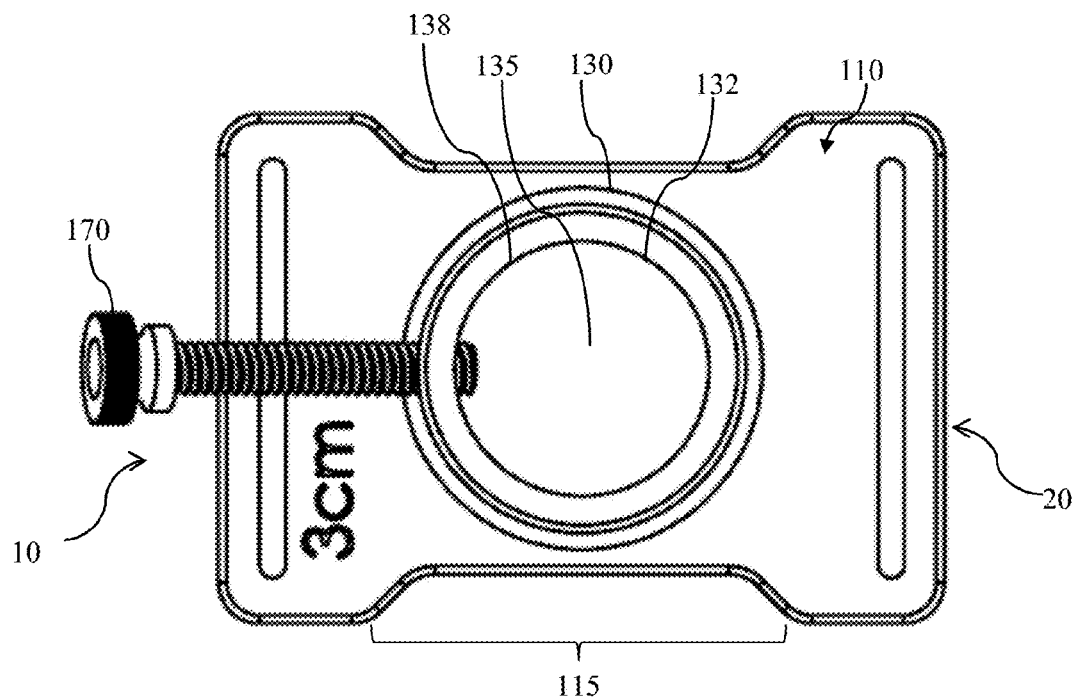
Figure 6C:
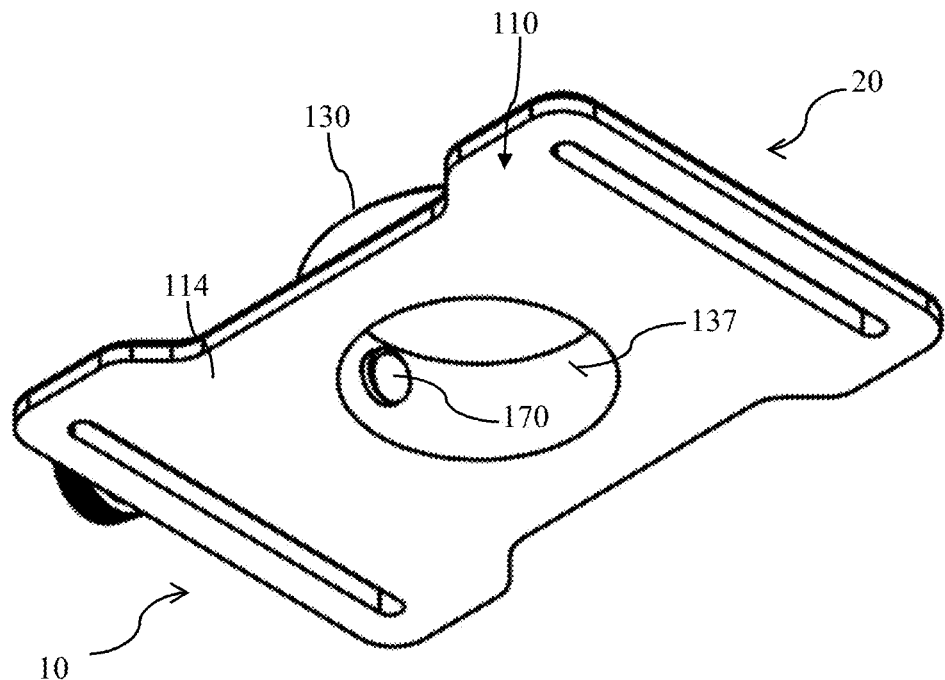
Figure 6D:
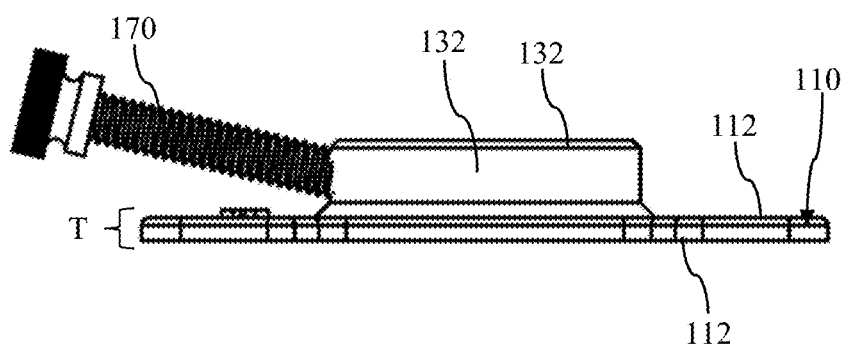
Figure 7A:
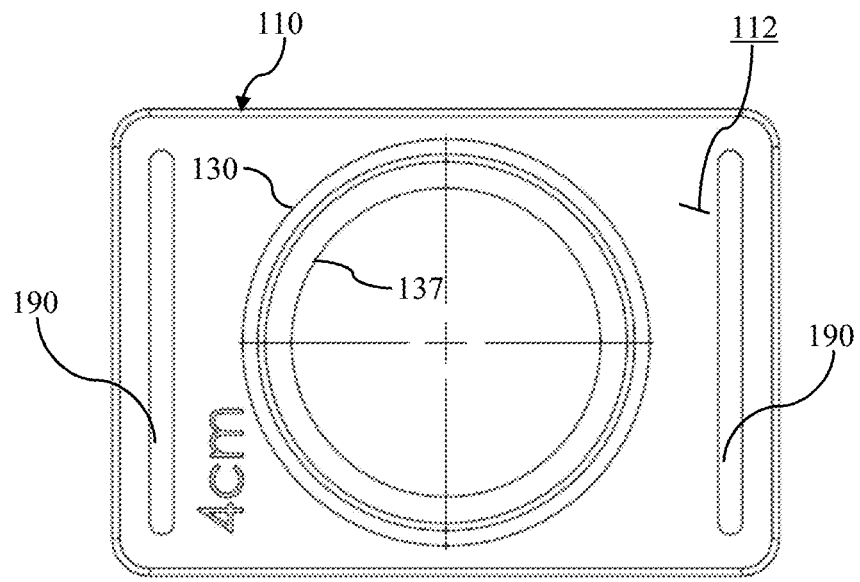
FIGS. 7A-7B illustrate an alternative embodiment, similar to that shown in FIGS. 6A-6D, with a larger orifice, where
Figure 7B:
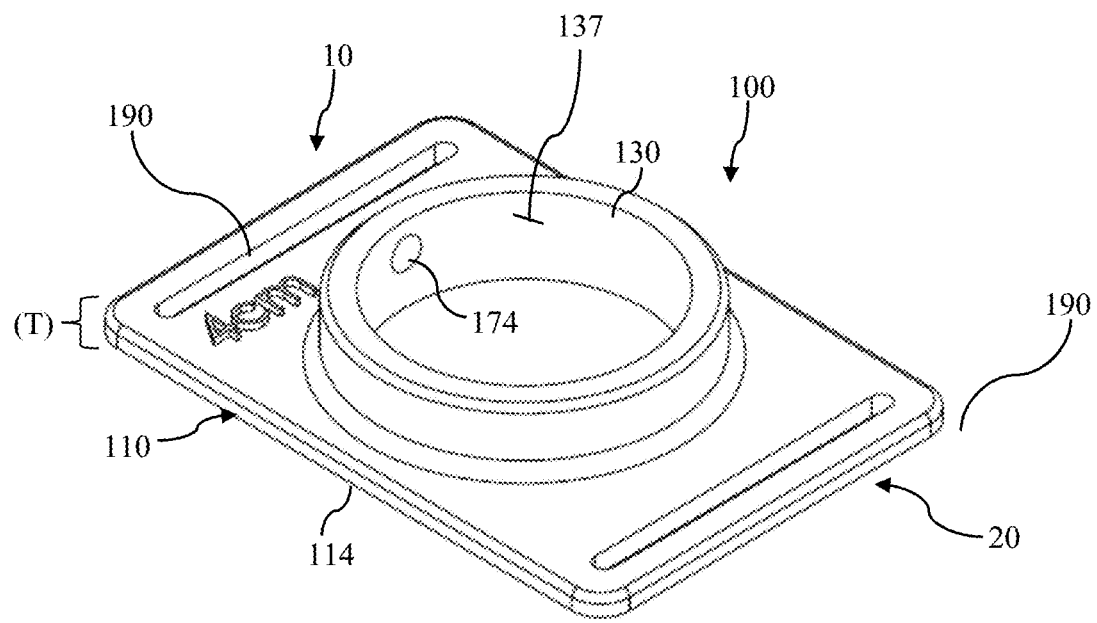

There could also be one or more structures on the bracket that facilitate attachment of one or more of the above-described devices or mechanisms. For example, a coupling device can be a structure or formation on the bracket to which a strap can be affixed, such as, by way of non-limiting example, a detent, dowel, hook, or other type of surface extension to which a strap can be directly attached or attached by one of the coupling devices mentioned above. FIG. 5B illustrates one example of this type of coupling. There could also be one or more arms or protrusions along one or more sides of the plate around which a strap can be affixed.

In one embodiment, a connector 190 can be one or more openings through the plate 110, such as, for example, slots, holes, or cut-outs through which a strap can be secured to the bracket. FIGS. 3A-C and 7A-B illustrate non-limiting examples of a bracket that has openings at either end of the plate. FIGS. 8B and 10A-10C illustrate one example of how the straps of a strapping girdle can be affixed, either permanently or removably, to the bracket using the connector openings. As will be discussed below, the straps themselves can have any of a variety of devices or fixtures for securing the ends of a strap after it has been passed through an opening. In a further embodiment, there can be more than one opening to allow for adjustment of the bracket. There can also be more than one type of connector utilized on a bracket. Thus, there may be one or more openings and one or more coupling devices or structures on the bracket for attaching one or more straps.

The purpose of an opening is to allow for the attachment of one or more straps of a strap system 200. Thus, it will be understood that a person with skill in the art will be able to determine numerous methods, devices, structures, and mechanisms by which one or more straps can be connected to a bracket. The figures illustrate only a few possible examples. Variations that provide the same function, in substantially the same way, with substantially the same result are within the scope of this invention.

To secure a bracket 100 to a patient, in particular to hold it against the perineum area or groin area of a patient, a strap apparatus 200 having one or more bands, straps, belts, suspenders, cords, or similar items can be used. Such items can be used to secure the bracket against the body, while simultaneously maintaining the position of a medical device emplaced in vivo or in a body cavity. While a bracket 100 of the subject invention is particularly suitable for use on or about the perineum area of the body, that does not imply that embodiments cannot be utilized on other areas of the body. Thus, the type or design of the strap apparatus and method of use in holding the bracket will vary depending upon location on the body. A person with skill in the art will be able to determine many other uses for a bracket and the type of strap system required to secure items on or within the body using a bracket of the subject invention.

In one embodiment, a strap apparatus is a straddling girdle 200 used to attach to the bracket and to secure the bracket against the perineum or groin area of a patient. When utilized together, the bracket and the straddling girdle can provide an immobilization system 300 for maintaining the position of a medical device emplaced in vivo. In particular, a medical device emplaced in vivo through or in the area of the perineum. Ideally, the straddling girdle has multiple points of adjustment to accommodate all sizes of patients and ensure that the bracket is properly placed on the body. It can also be helpful if the immobilization system is relatively comfortable to wear, as it will likely be placed directly against the skin.

A straddling girdle can include multiple components that are used to immobilize a bracket against the body. FIGS. 8A, 8B, 10A and 10B illustrate one embodiment of a straddling girdle. One component can be a waist strap 220 that initially secures the straddling girdle around the waist. A waist strap is, in general, a length of material that goes around the wait. It can be an adjustable loop, hoop, or ring of material that can be brought over the body and secured around the waist. Alternatively, it can be like a belt that includes two ends 222 that are brought together to close the waist strap over the waist and are also adjustable by any of a variety of methods, known to those with skill in the art. As will be disclosed, additional straps can be adjustably attached to the waist strap. Therefore, it can be beneficial if the additional straps can be adjustable on the waist strap as well. The waist strap or ends 222 thereof can be secured by any of a variety of methods and devices, including, but not limited to, hook and loop material, snaps, buckles, D-rings, clips, and other devices known to those with skill in the art. Alternatively, the ends 222 of the waist strap 220 can be overlapped and attached or they can be self-attachable, such that they loop back over themselves and attach to their own respective strap.

One embodiment employs a slider 230 to secure the waist strap and, as mentioned above, allows the ends 222 of the waist strap to be attached to their own strap. FIGS. 9A and 9B illustrate one embodiment of a slider, according to the subject invention. This embodiment utilizes a generally flat panel with two or more cutouts in which the ends 222 of a belt-like waist strap 220 can be put through and looped back over one side edge 237 so that the ends 222 can be attached to their respective straps. FIG. 10A illustrates one example of this where the left strap (labeled in the figure) is put through a cutout 235, looped over the side edge 237, and adjustably self-attached. Sliders are known in the art and utilized extensively to adjust similar such elongated straps on other devices and apparatuses. They can have various structures or features that make them amenable for the particular usage. Such variations can also be applied to the slider embodiments of the subject invention.

Figure 8A:
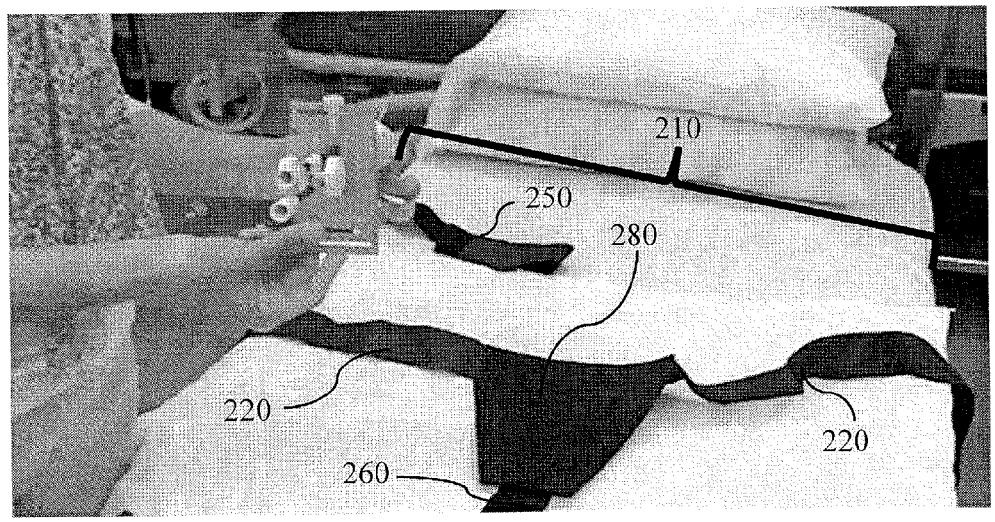
FIGS. 8A-8B are photographs of an embodiment of a strap apparatus as a strapping girdle (FIG. 8A) that can be used to position and hold a bracket embodiment of the subject invention in place on a patient (FIG. 8B).
Figure 8B:
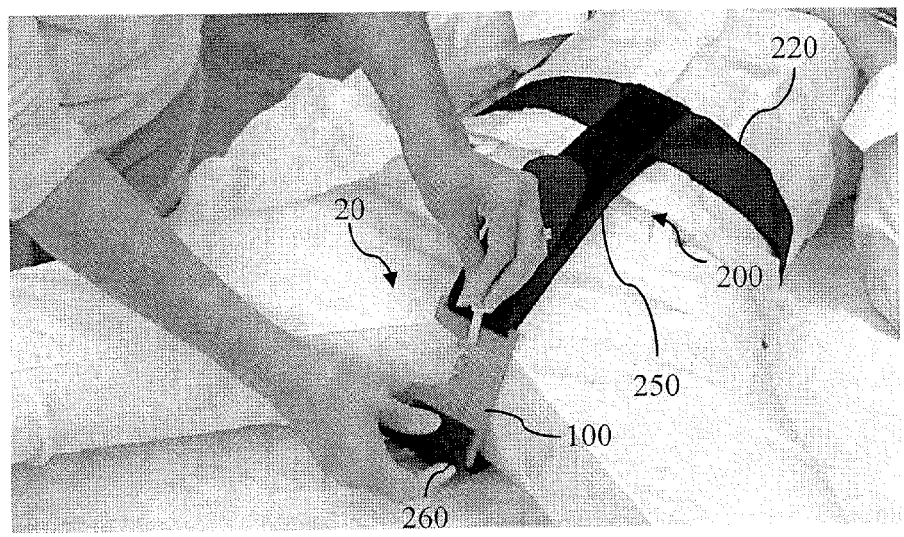

With regard to the straddling girdle 200, there can also be at least one anterior strap 250 and at least one posterior strap 260 that engage the bracket with the waist strap. An anterior strap can have a first end 252 that is adjustably attached to the waist strap. This can be accomplished in several ways known to those with skill in the art. One option is to have the first end 252 hooked or looped so that it slides on the waist band, an example of which is shown in FIG. 8B. Alternatively, when a slider 230 is utilized, the slider can have one or more additional cutouts 235 at the bottom end 238 of the slider. The first end 252 of the anterior strap can then be adjustably attached to the slider through one or more of the bottom end cutouts. One non-limiting example of this is shown in FIG. 10A. Multiple cutouts can provide additional adjustability to the immobilization system 300.

The bracket 100 can have multiple connectors 190 to which a second end 254 of the anterior strap 250 can be adjustably attached. Connector embodiments were discussed in detail above and are applicable to the attachment of the second end of an anterior strap. In a specific embodiment, shown, for example, in FIGS. 8B and 10A-10C, the connector is one or more openings through the plate through which the second end 254 of the anterior strap can be connected. FIGS. 8B and 10A-10C illustrate one example of this where the second end is passed through a connector opening, looped over the anterior end 10 of the bracket and reattaches to itself by any method or device known in the art, e.g., hook and loop material. This can impart adjustability to the strap and a positioning of the bracket and is relatively easy to implement when installing on a patient.

The factors that can be considered by those skilled in the art with regard to the choice of materials for each of the components of the subject invention have been discussed above and are reasserted here with regard to the bracket 100 and strap apparatus 200. In a particular embodiment, the bracket 100 is comprised of plastic and the strap apparatus 200 is comprised of cloth and Velcro. In a specific embodiment, the bracket and straps may be comprised of a variety of materials. Variations in material that provide the same functionality, in substantially the way as described herein, with substantially the same desired results, are within the scope of this invention.

Figure 11B:
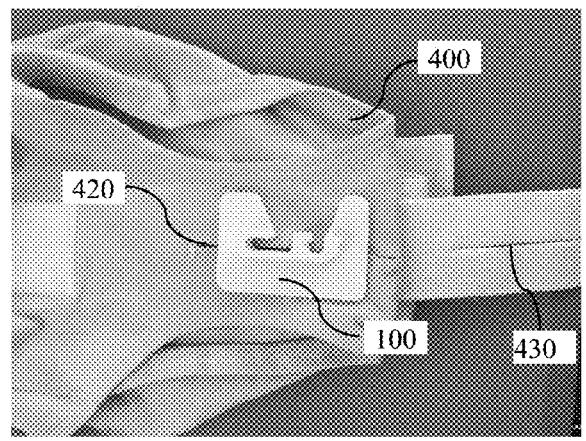
Figure 11C:
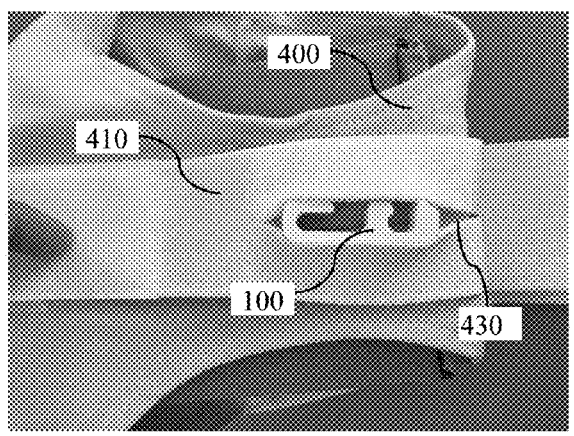
Figure 11D:
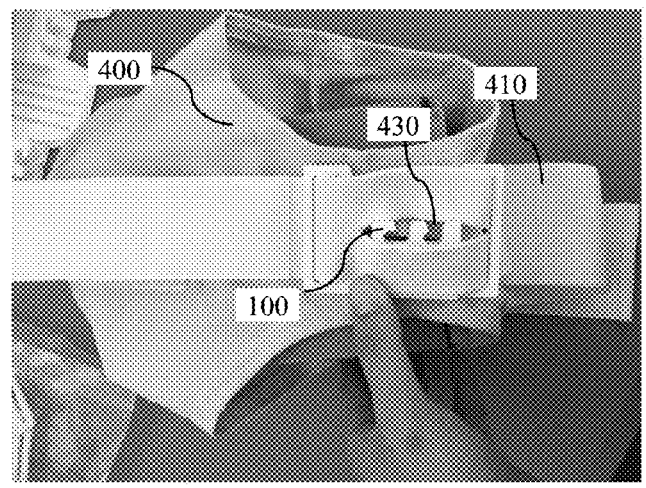

In an alternative embodiment, the strap apparatus 200 is a garment 400 that can be worn or wrapped around the groin and/or hips of a patient. For example, a strap apparatus can be a diaper- or brief-like garment that is wrapped around or pulled up around the hips, respectively. In a further embodiment, the garment has at least one groin strap 410 for securing a bracket 100. In a still further embodiment, the garment has at least one through hole 420 that allows a brachytherapy device to be passed through the bracket and the garment. In yet another embodiment, the at least one groin strap has a slit 430 through which the bracket can be accessed, when the groin strap is used to affix the bracket to the garment. FIG. 11A illustrates a non-limiting example of a garment that can be wrapped around the groin and hips of a patient. In this example, a bracket 100 can be incorporated or affixed into the area of the garment that covers the perineum or groin area of a patient, such that an additional groin strap is not required. FIGS. 11B, 11C, and 11D illustrate a non-limiting example of a brief style garment that includes a groin strap 410 for securing a bracket at the groin area. FIGS. 11C and 11D illustrate an example of a groin strap with a slit that can be used to hold a bracket in place against the groin area of the garment and/or the patient. FIG. 11D illustrates how the connectors 190 on a bracket 100 can be used with the groin strap on the garment to hold the bracket in place. Once the garment is in place on a patient, a medical device 50 can be inserted through the bracket and the through holes.

The components of this immobilization system 300 including but not limited to, the bracket 100, strap apparatus 200, and slider 230, may be reusable or disposable. The term "reusable" implies that the device may be used more than one time. The reusable device could potentially need to be sterilized without any adverse effects on the function of the device. The term "disposable" is used to indicate that the device will be used one time and subsequently disposed of appropriately.

Following is an example that illustrates procedures for practicing the subject invention. These examples are provided for the purpose of illustration only and should not be construed as limiting. Thus, any and all variations that become evident as a result of the teachings herein or from the following examples are contemplated to be within the scope of the present invention.

EXAMPLE 1

Method Utilizing the Immobilization System with a Tandem and Ring Device

A tandem and ring immobilization system is depicted in FIG. 10A. This immobilization system is designed in a diaper-like pattern that fits the patient's anatomy for stable immobilization. The entire device can be designed to be universal and disposable, avoiding the need for patient customization and cleaning.

The immobilization system shown in FIG. 10A includes a bracket that can immobilize the tandem and ring, a slider, and straps that engage with the slider and the bracket to fix the bracket position on the patient and prevent or at least inhibit rotation or translation of the bracket during the procedure. An enlarged view of the bracket is shown in FIG. 10B). This version of the bracket has two slotted receivers, the top one of which holds the tandem while the other holds the ring. The design can be universal so that all tandem-and-ring sets will fit. Once the tandem-and-ring set is properly placed into the receiver slots, a set screw can be tightened through a hole in the side of the bracket and into the top receiver slot to immobilize the tandem-and-ring in the receiver slots. By way of example, FIG. 10C shows a 60/60 tandem and 60/30 ring affixed to the bracket.

Before the tandem-and-ring is emplaced, the bracket should be positioned and secured on the patent. There can be a right-side strap, a left-side strap, a posterior straddling strap, and an anterior straddling strap. As shown, in FIGS. 10A-10C, each strap can be attached at one end to a posterior pad on which the patient lies and each strap has a fabric hook and loop fastener, but buckles or snaps could also be used. The right-side and left-side straps can be passed through two cut-outs, respectively, along the sides of the slider and the straps doubled-back on themselves to secure the position of the bracket. The anterior straddling strap can be passed through a third cut-out on the bottom of the slider and through a connector on the bracket and then doubled-back on itself to secure the bracket. Further, the posterior straddling strap can pass through another connector on the bottom of the bracket and, again, doubled-back to be secured and to secure the bracket position. By adjusting the straps, the bracket can be optimally placed on a patient and held in that optimal position throughout treatment. Furthermore, the adjustable design of the straps ensures that the immobilization system can tightly fit almost all patients. For extremely large patients, extension straps can be provided.

In a specific example of using the immobilization system the patient lies on her back on top of the posterior pad with legs spread apart. Then the right and left straps are fastened tightly around the patient's waist using the slider. The tandem-and-ring device can then be inserted into the patient and the hollow holders subsequently fixed to the bracket slots. The anterior straddling strap can be fastened to the anterior end of the bracket and the posterior straddling strap can be finally adjusted to secure the bracket around the patient's perineum region and fastened to the posterior end of the bracket. After additional adjustments to the straps, if necessary, the bracket is in position to hold the bracket and tandem-and-ring set tightly to the perineum. This configuration is able to fix the inserted tandem-and-ring to the patient's pelvis and prevents undesirable movement during the HDR procedure.

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

The examples and embodiments described herein are for illustrative purposes only and that various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

The invention has been described herein in considerable detail, in order to comply with the Patent Statutes and to provide those skilled in the art with information needed to apply the novel principles, and to construct and use such specialized components as are required. However, the invention can be carried out by specifically different equipment and devices, and that various modifications, both as to equipment details and operating procedures can be effected without departing from the scope of the invention itself. Further, although the present invention has been described with reference to specific details of certain embodiments thereof and by examples disclosed herein, it is not intended that such details should be regarded as limitations upon the scope of the invention except as and to the extent that they are included in the accompanying claims.

We claim:

1. An immobilization system comprising:
   a bracket, adapted to secure a medical device placed within a cavity in a body where some part of the medical device extends to an outside of the cavity, the bracket comprising,
      a plate having an anterior end and a posterior end,
      a channel wall on the plate that defines a receiver,
      a slot within the channel wall through which the part of the medical device extending from the cavity passes into the receiver,
      a bore through the channel wall that leads into the receiver,
      a brace operably connected to the bore, where the brace is configured to advance through the bore and into the receiver to contact and hold the medical device therein, a first connector at the anterior end of the plate and a second connector at the posterior end of the plate; and a strap apparatus, adapted to attach around the body, to secure the bracket to the outside of the body cavity.

2. The immobilization system according to claim 1, wherein the body cavity is a uterus and the medical device is a brachytherapy device having a part thereof securable within the receiver.

3. The immobilization system according to claim 2, comprising at least two receiver channels, wherein a first receiver channel is anterior to a second receiver channel.

4. The immobilization system according to claim 1, wherein the brace is a threaded screw.

5. The immobilization system according to claim 1, wherein the strap apparatus is a straddling girdle comprising:
   a waist strap,
   an anterior straddling strap that operably connects to the first connector and
   a posterior straddling strap that operably connects to the second connector.

6. The immobilization system according to claim 5, further comprising a slider having two or more cut-outs, wherein at least the waist strap is secured to at least one of the two or more cut-outs.

7. The immobilization system according to claim 6, wherein the anterior straddling strap is further operably connected to at least one of the two or more cut-outs.

8. The immobilization system according to claim 1, wherein the strap apparatus is a garment with at least one through hole through which the medical device extends to engage with the bracket receiver.

9. The immobilization system according to claim 8, further comprising at least one groin strap for securing the bracket to the garment.

10. The immobilization system according to claim 9, wherein the groin strap is operably connected to at least one of the connectors on the bracket.

11. A method for securing a medical device within a body cavity comprising:
    securing to an outside of the body cavity an immobilization device comprising,
    a bracket, adapted to secure the medical device placed within a cavity in a body where some part of the medical device extends to an outside of the cavity, the bracket comprising,
    a plate having an anterior end and a posterior end,
    a channel wall on the plate that defines a receiver,
    a slot within the channel wall through which the part of the medical device extending from the cavity passes into the receiver,
    a bore through the channel wall that leads into the receiver,
    a brace operably connected to the bore, where the brace is configured to advance through the bore and into the receiver to contact and hold the medical device therein,
    a first connector at the anterior end of the plate and a second connector at the posterior end of the plate; and
    a strap apparatus, adapted to attach around the body; utilizing the strap apparatus to secure the bracket to an outside of the body cavity,
    engaging the part of the medical device extending from the body cavity with the receiver in the bracket, and
    extending the brace through the bore and into the receiver until the brace contacts the part of the medical device within the receiver and until the part of the medical device within the receiver is secured in place.

12. The method according to claim 11, wherein the body cavity is a uterus and the medical device is brachytherapy device.

13. The method according to claim 11, wherein the brace is a threaded screw.

14. The method according to claim 11, wherein the strap apparatus is a straddling girdle comprising:
    a waist strap for attaching around a body,
    an anterior straddling strap that operably connects to the first connector and
    a posterior straddling strap that operably connects to the second connector wherein the method further comprises:
    positioning the straddling girdle with the straps laid open,
    securing the waist strap around the body,
    placing the medical device within the body cavity with the part of the medical device extending out from the body cavity,
    positioning the bracket over the body cavity,
    sliding the part of the medical device extending from the body cavity through the slot and into the receiver of the bracket,
    passing the anterior straddling strap and the posterior straddling strap through the respective first and second connectors of the plate, and securing the straps to hold the bracket and the part of the medical device in the receiver in place on the outside of the body cavity.

15. The method according to claim 11, wherein the strap apparatus is a garment worn around the body, where the garment has at least one through hole.

16. The method according to claim 15, further comprising at least one groin strap for securing the bracket to the garment.

17. The method according to claim 16, wherein the method further comprises passing the groin strap through at least one of the connectors on the plate.

18. The immobilization system, according to claim 17, further comprising a slit in the groin strap, through which a part of the medical device extends.

* * * * *